US008287922B2

(12) United States Patent
Chong et al.

(10) Patent No.: US 8,287,922 B2
(45) Date of Patent: Oct. 16, 2012

(54) **VAPORIZED *LOBELIA* PRODUCT AND METHOD OF USE**

(75) Inventors: Alexander ChinHak Chong, St. Louis Park, MN (US); William P. Bartkowski, Edina, MN (US); Marshall A. Thompson, Camarillo, CA (US)

(73) Assignee: Chong Corporation, Minneapolis, MN (US)

( * ) Notice: Subject to any disclaimer, the term of this patent is extended or adjusted under 35 U.S.C. 154(b) by 0 days.

(21) Appl. No.: 12/858,382

(22) Filed: Aug. 17, 2010

(65) Prior Publication Data

US 2011/0038961 A1  Feb. 17, 2011

Related U.S. Application Data

(60) Provisional application No. 61/234,562, filed on Aug. 17, 2009.

(51) Int. Cl.
*A61K 36/00* (2006.01)
(52) U.S. Cl. ..................... 424/725.1; 424/725
(58) Field of Classification Search ........................ None
See application file for complete search history.

(56) References Cited

U.S. PATENT DOCUMENTS

| 5,234,008 | A | | 8/1993 | Fagg | |
|---|---|---|---|---|---|
| 5,240,016 | A | | 8/1993 | Nichols et al. | |
| 5,486,362 | A | * | 1/1996 | Kitchell et al. | ............... 424/426 |
| 6,513,524 | B1 | | 2/2003 | Storz | |
| 2004/0031495 | A1 | | 2/2004 | Steinberg | |
| 2006/0204598 | A1 | | 9/2006 | Thompson | |
| 2007/0280652 | A1 | | 12/2007 | Williams | |
| 2008/0060663 | A1 | | 3/2008 | Hamade et al. | |
| 2008/0166303 | A1 | | 7/2008 | Tamarkin et al. | |
| 2008/0173300 | A1 | | 7/2008 | Justman | |
| 2008/0241255 | A1 | * | 10/2008 | Rose et al. | ................... 424/489 |
| 2008/0257367 | A1 | | 10/2008 | Paterno et al. | |
| 2009/0118331 | A1 | * | 5/2009 | Crooks et al. | ................. 514/317 |
| 2010/0242974 | A1 | | 9/2010 | Pan | |

FOREIGN PATENT DOCUMENTS

JP        60009462 A  *  1/1985

OTHER PUBLICATIONS

Wikipedia_Lobelia, Last modified Feb. 28, 2012, Retrieved from the Internet: <http://en.wikipedia.org/wiki/Lobelia>.
International Search Report for PCT/US2010/45806 dated Sep. 29, 2010.
International Search Report for PCT/US2010/045804 dated Oct. 14, 2010.

* cited by examiner

*Primary Examiner* — Qiuwen Mi
(74) *Attorney, Agent, or Firm* — Cislo & Thomas LLP

(57) ABSTRACT

In one embodiment, a method for *lobelia* delivery is provided comprising: providing a *lobelia* solution suitable for vaporization in a compact handheld device; providing the compact handheld device; vaporizing the *lobelia* solution at a low temperature upon activation by a user such that an effective serving of *lobelia* is provided to the user. In various aspects of this embodiment the *lobelia* solution comprises propylene glycol, water, alcohol and glycerin, the step of vaporizing the *lobelia* solution comprises using a vaporizer to vaporize the *lobelia* solution, and the effective serving of *lobelia* is provided to the user in less than 20 activations, less than 15 activations, less than 10 activations, less than 5 activations, or between about 8-10 activations.

19 Claims, No Drawings

VAPORIZED *LOBELIA* PRODUCT AND METHOD OF USE

CROSS-REFERENCE TO RELATED APPLICATIONS

This application claims the benefit of U.S. Provisional Patent Application No. 61/234,562, filed Aug. 17, 2009, which is incorporated by reference herein in its entirety.

BACKGROUND

Smokers report a number of difficulties with current smoking tonics and smoking substitutes on the market. Smoking tonics and substitutes refers to products that are used by smokers not looking to quit the activity, but instead have something that they can use or do which substitutes for or addresses the activity or condition in places or situations where they cannot smoke by law, regulation or common courtesy. Some of these products include gums, lozenges or smokeless devices that do not contain nicotine, which is often used in nicotine replacement therapies ("NRT") for smoking cessation. Government regulation of nicotine products is unclear. For example, the FDA is currently studying whether or not products containing nicotine can be sold without a new drug application ("NDA") and without going through clinical studies and a formal FDA approval process. Smoking tonics and substitutes are distinguished from FDA-approved smoking cessation products.

There are a number of traditional, established dietary supplement and/or herbal remedies that offer effective tonics or substitutions for smokers in environments where they otherwise cannot smoke. One of these is the herb *Lobelia*, also known as Indian Tobacco.

*Lobelia* is currently sold by herbalists and by retailers specializing in herbal remedies and dietary supplements as a "Respiratory Tonic." Descriptions of the herb in an online pharmacopeia published by the University of Maryland states this, "*Lobelia* (*Lobelia inflata*), also called Indian tobacco, may be used as an herbal remedy for respiratory conditions such as asthma, bronchitis, pneumonia, and cough. Native Americans historically have smoked *lobelia* as a treatment for asthma. In the 19th century, American physicians prescribed *lobelia* to induce vomiting in order remove toxins from the body. Because of this, it earned the name "puke weed." Today, *lobelia* is considered effective in helping clear mucus from the respiratory tract, including the throat, lungs, and bronchial tubes. Although few studies have evaluated the safety and effectiveness of *lobelia*, some herbalists today incorporate *lobelia* into a comprehensive treatment plan for asthma.

Various herbalists and naturalists have traditionally recommended that *lobelia* be vaporized using heat in order to avoid the by products of ignition and burning that accompany smoking and absorption of the herbal supplement. And, various retailers offer the advice to vaporize the supplement and sell heat implemented vaporizers. These vaporizers utilize heat to produce an ingestible vapor-like mist. And, these vaporizers are large, bulky and difficult to use in environments where smokers can no longer smoke, for example, social or workplace environments. As a result, *lobelia* vaporization is not considered a suitable or appropriate smoking tonic or substitute.

Accordingly there is a need in the art for an improved *lobelia* vaporization product and method of use.

SUMMARY

In one embodiment, a method for *lobelia* delivery is provided comprising: providing a *lobelia* solution suitable for vaporization in a compact handheld device; providing the compact handheld device; vaporizing the *lobelia* solution without the addition of heat for activation by a user such that an effective serving of *lobelia* is provided to the user. In various aspects of this embodiment the *lobelia* solution comprises propylene glycol, water, alcohol and glycerin, the step of vaporizing the *lobelia* solution comprises using a low temperature vaporization element to vaporize the *lobelia* solution, and the effective serving of *lobelia* is provided to the user in less than 20 activations, less than 15 activations, less than 10 activations, less than 5 activations, or between about 8-10 activations.

In another embodiment, a portable handheld device for *lobelia* delivery is provided comprising: a disposable cartridge, the disposable cartridge comprising a solution reservoir, the solution reservoir comprising a *lobelia* solution suitable for vaporization without the addition of heat to the *lobelia* solution; a vaporization mechanism releasable coupled to the disposable cartridge, wherein the vaporization mechanism vaporizes the *lobelia* solution at a low temperature to deliver an effective serving of *lobelia* to a user.

In another embodiment, a *lobelia* solution for use in a vaporization delivery mechanism comprising: water; alcohol; propylene glycol; and tincture of *lobelia*, wherein the *lobelia* solution is formulated such that it can be vaporized at a low temperature in a sufficient quantity to provide an effective serving of *lobelia* to a user.

In another embodiment, a disposable cartridge for use in a *lobelia* delivery device is provided comprising: a solution reservoir comprising a *lobelia* solution, wherein the *lobelia* solution is formulated such that it can be vaporized at a low temperature in a sufficient quantity to provide an effective serving of *lobelia* to a user.

Other features and advantages of the present invention will become apparent from the following detailed description. It should be understood, however, that the detailed description and the specific examples, while indicating the preferred embodiments of the present invention, are given by way of illustration only, since various changes and modifications within the spirit and scope of the present invention will become apparent to those skilled in the art from this detailed description.

DETAILED DESCRIPTION

In order to fully understand the manner in which the above-recited details and other advantages and objects according to the invention are obtained, a more detailed description of the invention will be rendered by reference to specific embodiments thereof.

In one embodiment, a *lobelia* delivery method is provided comprising providing a *lobelia* solution, and providing a mechanism for vaporization of the *lobelia* solution such that a user can absorb the vaporized solution via activation. Said embodiment is configured to deliver an effective serving of *lobelia* to a user. An active ingredient in the *lobelia* plant, lobeline, is similar to nicotine in its effect on the body. Like nicotine, it stimulates nerves in the central nervous system.

While an effective serving of *lobelia* may vary depending upon the particular physiology of the user, for example, the user's weight or body make-up, as used herein, the phrase means an amount sufficient such that the user experiences the intended positive effects experienced when *lobelia* is delivered through other known methods. In one aspect of this embodiment the effective serving can be delivered in as little as one activation by the user, and in other aspects the effective serving may be delivered through multiple activations by the user over 1, 2, 3, 4, 5, 6, 7, 8, 9, 10 or more minutes of use in a manner similar to the use associated smoking a tobacco product such as a cigarette or cigar.

Alternatively, the effective serving can be delivered over a specified number of activations by the user. Further, the number of activations can occur over a specified time period. For example, delivery of an effective serving can be provided with 1, 2, 3, 4, 5, 6, 7, 8, 9, 10, 11, 12, 13, 14, 15, 16, 17, 18, 19, or 20 activations. For example, the effective does may be delivered in 1-20 activations, 5-15 activations, 12-20, activations, 12-18 activations or about 15 activations, any of which can occur in a 1, 2, 3, 4, 5, 6, 7, 8, 9, 10, or 20 minute period. Some embodiments will be formulated and/or configured such that the effective does is delivered as quickly as possible, and other embodiments can be formulated and/or configured such that the effective does is delivered in about the same time and manner as if one was smoking a typical tobacco cigarette to simulate a typical smoking experience.

In various embodiments, a single serving may be delivered in less than 50 activations, about 1-50 activations, about 1-20 activations, 5-15 activations or about 8-10 activations. The single serving may include greater than 0.5 mg, between about 0.5-100 mg, between about 0.5-50 mg, between about 0.5-20 mg between about 0.5-10 mg between about 5-10 mg, or about 5 mg of *lobelia* solution.

In one aspect of this embodiment the *lobelia* solution comprises tincture of *lobelia*. In another aspect of this embodiment the *lobelia* solution is prepared by combining a tincture of *lobelia* with a first solution. In another aspect, the *lobelia* solution is prepared by contacting *lobelia* with a first solution. In another aspect of this embodiment, the first solution comprises one or more of water, alcohol, flavoring, and an inert non-reactive compound, e.g., propylene glycol, such that the *lobelia* solution can be vaporized for activation by a user. The first solution can comprise about 0.01%-20% water, 2-18% water, 5-15% water, or about 10% water, about 0.01%-20% alcohol, 2-18% alcohol, 5-15% alcohol, or about 10% alcohol, with the balance being propylene glycol. In another aspect of this embodiment, the solution further comprises glycerin, including from about 1-30%, 5-20%, 5-10%, or 10-15% glycerin.

Without being limited by theory, it is believed that the addition of glycerin provides a more robust vapor upon vaporization of the product.

In some embodiments the *lobelia* solution is formulated such that an effective serving of *lobelia* can be delivered to a user in a specified time period when the *lobelia* solution is vaporized and inhaled by a user. In one aspect of this embodiment the effective serving can be delivered over a specified time period when the solution is vaporized without the addition of heat.

In other embodiments the first solution may be any solution sufficient to form a *lobelia* solution such that the *lobelia* solution can be vaporized for activation by a user.

In another embodiment, a *lobelia* delivery method is provided comprising contacting *lobelia* with a first solution such that the constituents of the *lobelia* leach or are extracted to form a *lobelia* solution. The *lobelia* solution is then vaporized by a vaporization mechanism and inhaled by the user.

To promote the leaching or extracting of the constituents of the *lobelia* to form the *lobelia* solution, various methods may be employed to contact the *lobelia* with the solution, including maximizing the surface area of the *lobelia*. In one embodiment the *lobelia* is formed in the shape of a mesh screen through which a first solution is passed. In other configurations, the *lobelia* is formed to provide the maximum surface area for contact with the first solution yet still allow flow of the first solution through *lobelia* and into a vaporization mechanism. Examples of other configurations for use in maximizing the surface area of the *lobelia* for contact with a first solution include spirally wound *lobelia*, *lobelia* pellets, and *lobelia* powder, or encapsulating the *lobelia* in a porous, filter-like material, which will allow the solution to flow through the *lobelia*-encapsulate and the constituents of the *lobelia* to leach into the solution. Leaching and or extracting may also be promoted through modifying the temperature of the first solution or the pressure under which the first solution is contacted with the *lobelia*.

In some embodiments the first solution and the *lobelia* are contacted immediately prior to vaporization. In other embodiments the first solution and *lobelia* can be contacted over an extended period of time prior to vaporization. For example, the *lobelia* can be provided immersed in the first solution such that the first solution has been in contact with the *lobelia* for an extended period of time prior to vaporization. In said examples, the leaching or extraction of the *lobelia* constituents can be promoted by varying the conditions or other parameters during contact of the first solution with the *lobelia*. The *lobelia* can be removed from the formed *lobelia* solution prior to providing the *lobelia* solution to the end consumer for inclusion in a device for vaporization, or immediately prior to vaporization by draining the *lobelia* solution from the *lobelia*.

The *lobelia* solution is then vaporized for activation by the user. One example of a mechanism that may be used to vaporize the *lobelia* solution is disclosed in U.S. patent application Ser. Nos. 10/587,707 and 10/547,244, incorporated herein by reference. Other mechanisms may be used which including atomizers or other vaporizers known in the art or combinations thereof. Vaporization or atomization can be performed with or without the additional of heat to the solution. For example, the solution to be vaporized can first be atomized providing for ease of vaporization without the addition of heat. In one aspect a low temperature vaporizer is provided, including vaporization at temperatures from about 180° C. to about 280° C., from about 180° C. to about 250° C., from about 180° C. to about 225° C., from about 180° C. to about 200° C., wherein the temperature indicates the temperature at which the solution is vaporized. It is understood that the temperature of the vaporization element may be higher.

In another embodiment, a device for implementing the *lobelia* delivery methods set forth herein is provided comprising a shell, a mouthpiece, an air inlet provided on the external wall of the shell; a cell, an electronic circuit board, a normal pressure cavity, a sensor, an atomizer, a solution reservoir; a *lobelia* reservoir, a solution stream passage, a negative pressure cavity provided in the sensor, an atomization cavity arranged in the atomizer, and an aerosol passage, wherein the solution reservoir is in contact with the *lobelia* reservoir and the atomizer, and the air inlet, normal pressure cavity, atomizer, aerosol passage, gas vent and mouthpiece are interconnected.

In another embodiment, a device for implementing the *lobelia* delivery methods set forth herein is provided comprising a shell, a mouthpiece, an air inlet provided on the external wall of the shell; a cell, an electronic circuit board, a normal pressure cavity, a sensor, an atomizer, a solution reservoir; a solution stream passage, a negative pressure cavity provided in the sensor, an atomization cavity arranged in the atomizer, and an aerosol passage, wherein the solution reservoir is in contact with the atomizer, and the air inlet, normal pressure cavity, atomizer, aerosol passage, gas vent and mouthpiece are interconnected. The solution reservoir may be configured to retain a *lobelia* solution and *lobelia*, or *lobelia* solution that has previous been contacted with *lobelia*.

In some embodiments the device is provided in the configuration of a cigar or cigarette. In other embodiments the device is provided in other configurations such that the device can be readily distinguished from a cigar or cigarette.

In some embodiments, the delivery device is a hand-held, personal portable device that is disposable. Moreover, in some embodiments the method of vaporization does not use heat, rather it uses piezoelectric elements to atomize the *lobelia* solution.

Some embodiments provided herein produce a vapor containing the key constituents of *lobelia* without components created through burning the *lobelia*. Moreover, said embodiments do not create "second hand smoke" or have other possible negative social appearances.

In another embodiment, a *lobelia* solution is provided for use in the methods and devices disclosed herein. The *lobelia* solution comprises *lobelia* constituents in a form suitable for vaporization. The *lobelia* solution may be formed by contacting a first solution as set forth herein with *lobelia* as set forth herein to form a *lobelia* solution. The concentration of the *lobelia* constituents of the *lobelia* solution can be varied by varying the method for making the *lobelia* solution. For example, one can vary the contact time between the first solution and the *lobelia*, the temperature at which the contact occurs, or the pressure at which the contact occurs. The *lobelia* solution may be provided with or without *lobelia* in contact with the *lobelia* solution.

In another embodiment, a *lobelia* solution is provided comprising a tincture of *lobelia* combined with a first solution as set forth herein to form a *lobelia* solution suitable for vaporization for use in the methods and devices set forth herein.

In another embodiment a disposable cartridge is provided comprising a *lobelia* solution or *lobelia* and a first solution as set forth herein. The cartridge can include one or more servings of *lobelia* as set forth herein. In one aspect of this embodiment the cartridge can include between about 5-50 servings, between about 5-25 servings, between about 10-25 servings, between about 10-50 servings, between about 10-20 servings of *lobelia*.

Accordingly, some embodiments herein provide smokers or other users with an easy-to-use, convenient *lobelia* product. Said embodiments will provide smokers an easy-to-use, convenient and cost-effective smoking substitute that effectively replicates the physical attributes of smoking tobacco with a formulation that is both legal, from a regulatory standpoint, and effective as a respiratory tonic for smokers. Additionally, some embodiment also provide bronchial dilation that will provide temporary respiratory relief for conditions due to bronchitis and asthma.

Although the invention has been described with respect to specific embodiments and examples, it will be readily appreciated by those skilled in the art that modifications and adaptations of the invention are possible without deviation from the spirit and scope of the invention. Accordingly, the scope of the present invention is limited only by the following claims.

The invention claimed is:

1. A method for *lobelia* delivery comprising:
providing a *lobelia* solution suitable for vaporization in a compact handheld device;
providing the compact handheld device;
vaporizing the *lobelia* solution at a low temperature upon activation by a user such that an effective serving of *lobelia* is provided to the user, wherein the low temperature is from approximately 180 degrees C. to approximately 280 degrees C., wherein the *lobelia* solution further comprises water at a concentration of approximately 0.01% to approximately 20%, alcohol at a concentration of approximately 0.01% to approximately 20%, glycerin at approximately 1% to approximately 30%, and propylene glycol.

2. The method of claim 1 wherein the step of vaporizing the *lobelia* solution comprises using a low temperature vaporizer element to vaporize the *lobelia* solution at the low temperature.

3. The method of claim 2 wherein the effective serving of *lobelia* is greater than 0.5 mg.

4. The method of claim 2 wherein the effective serving of *lobelia* is from approximately 0.5 mg to approximately 100 mg.

5. The method of claim 2 wherein the effective serving of *lobelia* is from approximately 0.5 mg to approximately 50 mg.

6. The method of claim 2 wherein the effective serving of *lobelia* is from approximately 0.5 mg to approximately 20 mg.

7. The method of claim 2 wherein the effective serving of *lobelia* is from approximately 5 mg to approximately 10 mg.

8. The method of claim 1 wherein the *lobelia* solution comprises water at a concentration of approximately 2% to approximately 18%.

9. The method of claim 1 wherein the *lobelia* solution comprises water at a concentration of approximately 5% to approximately 15%.

10. The method of claim 1 wherein the *lobelia* solution comprises alcohol at a concentration of approximately 2% to approximately 18%.

11. The method of claim 1 wherein the *lobelia* solution comprises alcohol at a concentration of approximately 5% to approximately 15%.

12. The method of claim 1 wherein the *lobelia* solution comprises glycerin at a concentration of approximately 5% to approximately 20%.

13. The method of claim 1 wherein the *lobelia* solution comprises glycerin at a concentration of approximately 5% to approximately 10%.

14. The method of claim 1 wherein the *lobelia* solution comprises glycerin at a concentration of approximately 10% to approximately 15%.

15. The method of claim 1 wherein the low temperature ranges from approximately 180 degrees C. to approximately 250 degrees C.

16. The method of claim 1 wherein the low temperature ranges from approximately 180 degrees C. to approximately 225 degrees C.

17. The method of claim 1 wherein the low temperature ranges from approximately 180 degrees C. to approximately 220 degrees C.

18. The method of claim 1 wherein the *lobelia* solution is provided in a disposable cartridge to consistently deliver the effective serving of *lobelia* per activation.

19. The method of claim 1 wherein the *lobelia* solution is extracted from *lobelia* that is configured to maximize a surface area of the *lobelia*, wherein the configuration is selected from the group consisting of *lobelia* in a shape of a mesh screen, *lobelia* that is spirally wound, *lobelia* in pellet form, *lobelia* in powder form, and *lobelia* encapsulated in a filter-like material.

* * * * *